United States Patent
Sime

(10) Patent No.: US 10,612,046 B2
(45) Date of Patent: *Apr. 7, 2020

(54) PLANT ACTIVATOR COMPOSITION

(71) Applicant: Rhizoflora, Inc., Santa Rosa, CA (US)

(72) Inventor: Alan David Sime, Santa Rosa, CA (US)

(73) Assignee: Rhizoflora Inc., Sebastopol, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/279,592

(22) Filed: Feb. 19, 2019

(65) Prior Publication Data

US 2019/0211363 A1    Jul. 11, 2019

Related U.S. Application Data

(60) Continuation of application No. 15/429,794, filed on Feb. 10, 2017, now Pat. No. 10,287,609, which is a division of application No. 14/576,180, filed on Dec. 18, 2014, now abandoned.

(60) Provisional application No. 61/918,422, filed on Dec. 19, 2013.

(51) Int. Cl.
| | |
|---|---|
| *C12P 5/00* | (2006.01) |
| *A01N 65/00* | (2009.01) |
| *A01N 65/08* | (2009.01) |
| *A01N 65/36* | (2009.01) |
| *A01N 65/40* | (2009.01) |

(52) U.S. Cl.
CPC ............. *C12P 5/007* (2013.01); *A01N 65/00* (2013.01); *A01N 65/08* (2013.01); *A01N 65/36* (2013.01); *A01N 65/40* (2013.01)

(58) Field of Classification Search
None
See application file for complete search history.

(56) References Cited

U.S. PATENT DOCUMENTS

| | | | |
|---|---|---|---|
| 4,167,559 | A | 9/1979 | Michel |
| 4,339,432 | A | 7/1982 | Ritchey et al. |
| 4,952,392 | A | 8/1990 | Thame |
| 5,186,722 | A | 2/1993 | Cantrell |
| 5,294,434 | A | 3/1994 | King et al. |
| 5,514,779 | A | 5/1996 | Broekaert et al. |
| 7,279,151 | B2 | 10/2007 | Pushpangadan et al. |
| 7,350,331 | B1 | 4/2008 | Gontier et al. |
| 10,287,609 | B2 * | 5/2019 | Sime ............... C12P 5/007 |
| 2003/0092574 | A1 | 5/2003 | Munoz |
| 2004/0035162 | A1 | 2/2004 | Williams |
| 2005/0153005 | A1 | 7/2005 | Hysmith |
| 2007/0131010 | A1 | 7/2007 | Binder et al. |
| 2008/0146444 | A1 | 6/2008 | Fabri et al. |
| 2014/0274707 | A1 | 9/2014 | Thompson |

FOREIGN PATENT DOCUMENTS

| | | |
|---|---|---|
| WO | 1990/000193 A1 | 1/1990 |
| WO | 2000/042200 A1 | 7/2000 |
| WO | 2010/004584 A2 | 1/2010 |
| WO | 2013/039937 A1 | 3/2013 |

OTHER PUBLICATIONS

Whitmer et al. Influence of precursor availability on alkaloid accumulation by transgenic cell 2-6 line of Catharanthus reseus. Plant Physiol. Feb. 1998. vol. 116. No. 2. pp. 853-857 especially, Abstract, p. 856, col. 2, para 2; p. 854, col. 2, para 3.

Schulte et al. Mevalonate kinase activity in Catharanthus roseus plants and suspension cultured cells. Plant Science. 2000. vol. 150. pp. 59-69, especially, Abstract; p. 60, col. 2, para 1.

Smith "The magic of Yucca" Sep. 19, 2013 [online] [Retrieved on Apr. 7, 2015) Retrieved Y from website <URL:http://www.gardenandgreenhouse.netlindex.php/past-issues-mainmenu18/146-2013-garden-greenhouse/november-december-2013/1669-the-magic-of-yucca> especially p. 1, para 1.

Yang et al. Cell. Mol. Life Sci. vol. 70 pp. 1937-1948. (Year: 2012).

Maes et al. Plant Signaling and Behavior vol. 5 No. 2. pp. 205-207. (Year: 2010).

Nguyen et al. In Vitro Cell. Dev. Biol.-Plant. vol. 47 pp. 329-338. (Year: 2011).

Rahman et al. Malaysian Journal of Pharmaceutical Sciences vol. 1 pp. 39-49. (Year: 2003) (see abstract).

Goswami, Shambaditya, «Preliminary Phytochemical Screening and Standardisation of Leaves (5 )F *Catharanthus roseus* (L.) Indian Journal of Research in Pharmacy and Biotechnology, vol. 1 Issue 1, 2013).

Da Gloria (Pesq. agropec. bras., Brasilia V 35 n. 4 pp. 727-732: publication year 2000) (See p. 728right column, 2nd Paragraph and p. 729, right column, first full paragraph).

* cited by examiner

*Primary Examiner* — Katherine Peebles
(74) *Attorney, Agent, or Firm* — Edward S. Sherman

(57) ABSTRACT

A plant activator composition increases the concentration of terpenes and terpinoids in aromatic plant oils, and hence resulting in an increased concentration of terpene and terpinoids in the harvested dried plant or fruit. The composition contains one of more bio-active compounds that are optionally extracted from plants selected from one or more of the group consisting of mango, citrus (including grapefruit), *Catharanthus roseus* and *Pelargonium odoratissimum*, but alternatively may include one or more synthetic compounds selected from the group consisting of geranyl acetate, geraniol, beta-sitosterol, alpha-amyrin, beta amyrin, carotenoid, geranyl acetate, alpha-humulene, mevalonate kinase and geranyl. Depending on the type of plant being treated, the formulation is added during watering and feeding in optimum doses during the vegetative growth, flowering, and fruit set and/or swell stages.

20 Claims, 4 Drawing Sheets geraniol geranyl acetate geranyl mevalonic acid geranyl phosphate alpha-humulene beta amyrin beta-sitosterol alpha-amyrin

PLANT ACTIVATOR COMPOSITION

CROSS REFERENCE TO RELATED APPLICATIONS

The present application is a Continuation of and claims the benefit of priority to application with Ser. No. 15/429,794, filed on Feb. 10, 2017, which is in turn a Division of and claims the benefit of priority to the U.S. Non-provisional patent application Ser. No. 14/576,180 that was filed on Dec. 18, 2014, and is incorporated herein by reference.

The present application also claims the benefit of priority to the US Provisional Patent Application of the same title that was filed on Dec. 19, 2013, having application No. 61/918,442 and is incorporated herein by reference.

BACKGROUND OF INVENTION

The field of inventions is plant feeding compositions, and in particular a plant feed for increasing the plants synthesis of plant oils and in particular terpenoid compounds, and methods of synthesizing the same via plant cells, and extraction of the same.

Some types of plant oils have terpenes, related terpenoids, including isoprenoid or compounds that contain very interesting odor molecules. More specifically, terpenoids are unsaturated hydrocarbons in aromatic plant resins, which also act as natural preservatives and protectors, and generally consist of repeating units of a 5-carbon structure called isoprene. Many plants incorporate aromatic compounds that produce a plethora of odors that have been long thought to affect our physiology through odor activation (aromatherapy). Two of these odor molecules are limonene and myrcene. These occur in a wide variety of oil producing plants, and can be described to smell like lemons and grapefruit, respectively.

Many researchers have been aware of the power of odor chemistry to affect our moods, for example, many people describe a feeling of "sunny happiness" when smelling limonene. These types of compounds end up in the glands that inhabit the "skin" of plants, and can create biological affects in our bodies when ingested. For example, the plant oils in mint can cause a feeling of relaxation when taken as a cup of tea. Terpenoids also have a long history of being antimicrobial, capable of destroying or inhibiting the growth of disease-causing microbes and preventing infections.

Terpenoids compounds are hence widely used in perfume formulation, flavoring and medicinal compositions. They are produced in varying degrees by many plan species, and may be expressed in foliage, flower and fruit, many of which are edible.

To the extent such compounds have value independent of the plant, that is as a component of essential oils and flavoring and cannot be easily derived from synthetic chemical routes, it would be significant economic advantage to increase the yield of these compounds relative to the same input and use of soil, water, sun exposure and fertilizer as to grow unenhanced plants.

To the extent such compounds enhance the flavor, odor and aroma of plants, it would be desirable to increase the percentage of the same to enhance these properties, creating plants and foods with greater consumer appeal and enhanced value.

The above and other objects, effects, features, and advantages of the present invention will become more apparent from the following description of the embodiments thereof taken in conjunction with the accompanying drawings.

SUMMARY OF INVENTION

In the present invention, the first object is achieved by providing a process for plant production, the process comprising the steps of providing an extract of a pre-metabolite of a bio-active compound from at least one of the buds, flowers, bark, foliage and fruit of a first plant species, applying a composition of matter containing the extract of the pre-metabolite to a second plant species during the growth thereof, harvesting at least one of the buds, flowers, bark, foliage and fruit of the second plant species, wherein the composition of matter comprises floral alcoholic extracts of *Catharanthus roseus, C. longifolius, C. ovalis, Vinca minor* and *Pelargonium odoratissimum*, and a plant nutrient composition comprising one or more sources of carbohydrate in an amount sufficient to provide excess carbohydrate over that in the floral extract.

Another aspect of the invention is such a process wherein the composition of matter further comprises one or more floral alcoholic extracts of a plant selected from the group consisting of mango and citrus.

Another aspect of the invention is any such process wherein the composition of matter further comprises a plant enzyme.

Another aspect of the invention is any such process wherein the plant enzyme is mevalonate kinase.

Another aspect of the invention is any such process wherein the composition of matter further comprises a stabilizer selected from the group consisting of EDTA, sorbitol, methyl paraben and potassium sorbate.

Another aspect of the invention is any such process wherein the composition of matter further comprises one or more of sugars and disassociated sugars and potassium compounds, phosphorus compounds and amino acids.

Another aspect of the invention is any such process wherein the composition of matter further comprises one or more of sugars and disassociated sugars and potassium compounds, phosphorus compounds and one or more of L-glycine, L-luecine, L-glutamine and L-cysteine, nicotinic acid, thiamine HCl, and pyroxidine HCl.

Another aspect of the invention is a process for plant production, the process comprising the steps of providing an extract of a pre-metabolite of a bio-active compound from at least one of the buds, flowers, bark, foliage and fruit of a first plant species, applying a composition of matter containing an extracted pre-metabolite to a second plant species during the growth thereof, harvesting at least one of the buds, flowers, bark, foliage and fruit of the second plant species, wherein the composition of matter comprises a floral alcoholic extract of one or more of *Catharanthus roseus, C. longifolius, C. ovalis, Vinca minor* and *Pelargonium odoratissimum*, a plant nutrient composition comprising one or more sources of carbohydrate, to provide excess carbohydrate over that in the floral extract, one or more floral alcoholic extracts of a plant selected from the group consisting of mango and citrus, a stabilizer selected from the group consisting of EDTA, sorbitol, methyl paraben and potassium sorbate, and comprises yucca extract.

Another aspect of the invention is any such process further comprising the step of extracting one or more terpene compounds from the second plant species.

Another aspect of the invention is any such process wherein the composition of matter is applied during irrigation with water, and the amount of the composition of matter is initially applied at a first rate and then applied at second rate that is higher than the first rate.

Another aspect of the invention is any such process wherein the composition of matter is applied at the first rate during vegetative growth and before flowering occurs and then is applied at the second rate after flowering occurs.

Another aspect of the invention is any such process wherein the composition is applied at the first rate during vegetative growth and at the second rate during the last three weeks of flowering before seed set.

Another aspect of the invention is any such process wherein the composition is applied the first rate during reproductive fruit set and then applied at the second rate during the last four weeks of fruit development.

Another aspect of the invention is any such process further comprising the steps of culturing callus cells of the first plant species wherein the extract of a pre-metabolite of the bio-active compound from at least one of the bark, stems, foliage, buds, flowers and fruit of a first plant species is provided by extraction from the cultured callus cells of the first species.

Another aspect of the invention is any such process further comprising the step of separating protoplant cells from the first plant species and propagating the protoplast cells to create the callus cells.

Another aspect of the invention is any such process wherein the first plant species is one or more of *Catharanthus roseu, C. longifolius, C. ovalis, Vinca minor* and *Pelargonium odoratissimum*.

Another aspect of the invention is any such process further comprising the step of enzymatic digestion of cellulosic material to liberate the protoplast cells that are separated.

Another aspect of the invention is any such process further comprising the step of extracting one or more terpene compounds from the second plant species.

The above and other objects, effects, features, and advantages of the present invention will become more apparent from the following description of the embodiments thereof taken in conjunction with the accompanying drawings.

DETAILED DESCRIPTION

A plant activator composition increases the concentration of terpenes and terpenoids in aromatic plant oils, and hence resulting in increased concentration terpenes and terpenoids in the harvested dried plant or fruit. The composition preferably contains one of more bio-active compounds that are optionally extracted from plants selected from one or more of the group consisting of mango, citrus (including grapefruit), *Catharanthus roseus, C. longifolius, C. ovalis, Vinca minor, Phaseouls vulgaris* and *Pelargonium odoratissimum*. Not wishing to be bound by theory, it is believed that the plant extracts described herein contain a potent mixture of terpenoids and terpene compounds and related enzymes that are enhance the plant metabolism to increase terpene and terpenoids production. Hence, the plant extracts disclosed herein, as well as combinations of synthetic compounds of similar composition, will be referred to as bio-active terpenoids pre-metabolites.

Figure 1:
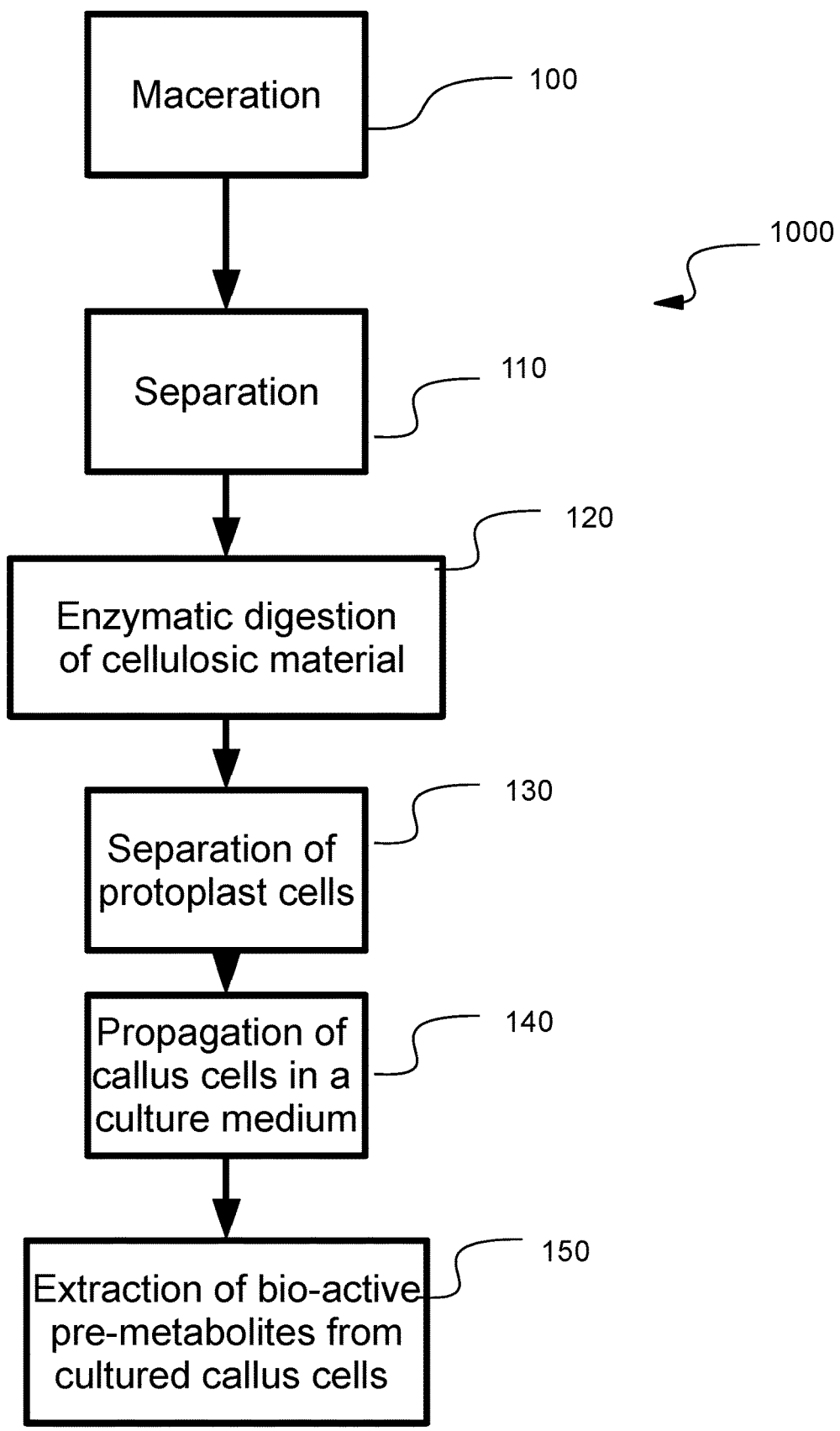
FIG. 1 is a flow chart illustrating the steps in one aspect of the invention in which a cell culture method is used to produce one of more bio-active pre-metabolites.

As plant callus cells are rich in the bio-active terpinoid pre-metabolites, another aspect of the invention, illustrated in FIG. 1, is the growth of callus cells using protoplast cells, which are then harvested for use in preferred formulations. The preferred plant extracts are believed to contain a mixture of terpenes, terpenoids, polyterpenes, cyclic polyterpines, including terpenoids of polyterpenes, cyclic polyterpenes, such as terpene phenolic compounds, as well as plant enzymes.

More specifically, the plant extract preferably include compounds selected from the group consisting of geranyl acetate, geraniol, geranyl phosphate, beta-sitosterol, alpha-amyrin, beta amyrin, carotenoid, alpha-humulene, mevalonate kinase, Mevalonic acid, and geranyl diphosphate.

Depending on the plant species used, and the extract composition, it may be augmented with one or more plant derived or synthetic compounds selected from the group consisting of geranyl acetate, geraniol, geranyl, beta-sitosterol, alpha-amyrin, beta amyrin, carotenoid, alpha-humulene, mevalonate kinase, Mevalonic acid, and geranyl diphosphate.

Figure 2:
FIG. 2 provides the chemical structure of select bioactive terpenoids compounds described as alternative to plant extracts in the specification, notably geranyl acetate, geraniol, geranyl phosphate, mevalonic acid, and alpha-humulene.
Figure 2:
Figure 2:
Figure 2:
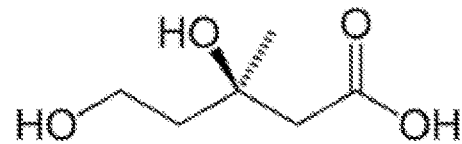
Figure 2:
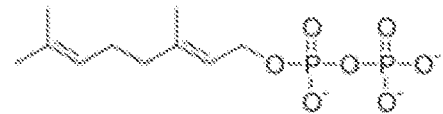
Figure 2:
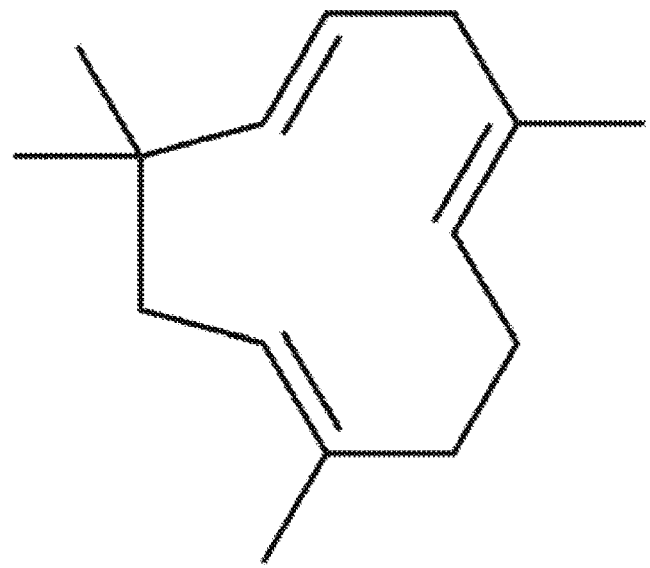
Figure 3:
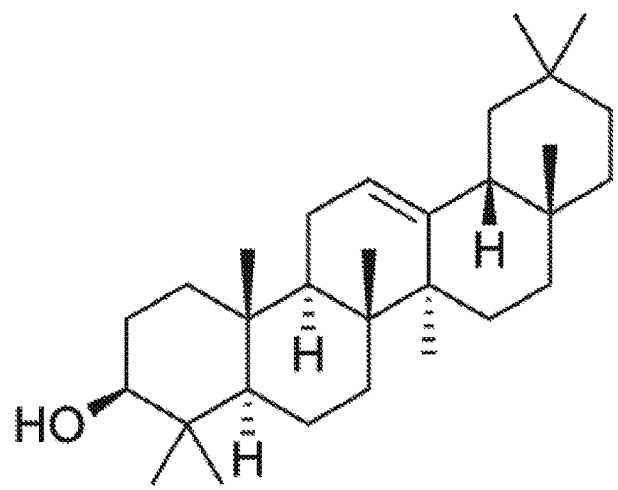
FIG. 3 provides the chemical structure of select bioactive terpenoids compounds described as alternative to plant extracts in the specification, notably beta amyrin, alpha-amyrin and beta-sitosterol.
Figure 3:
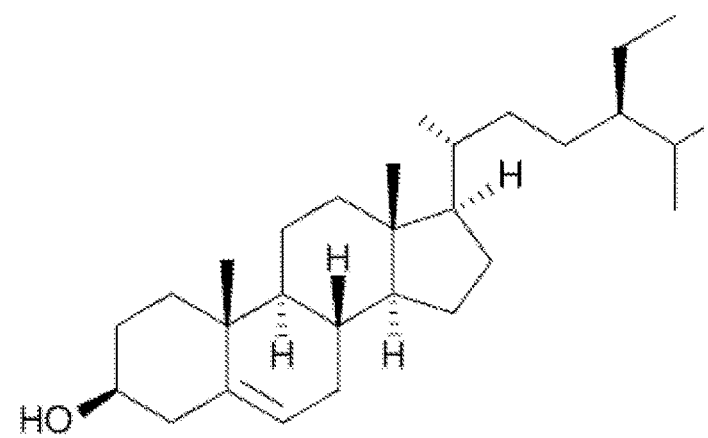
Figure 3:
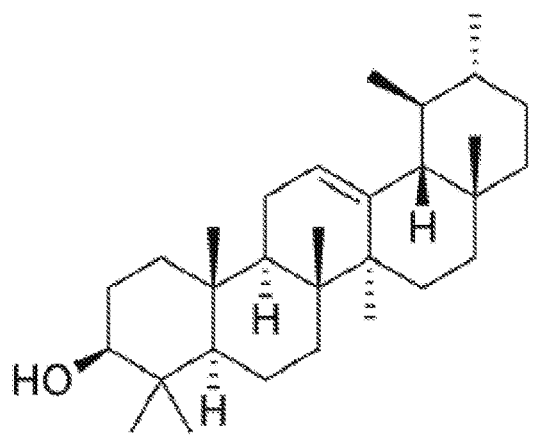

FIG. 2 and FIG. 3 provide the chemical structure of some of these preferred pre-metabolite compounds, which include terpenes, terpenoids, polyterpenes, cyclic polyterpines, including terpenoids of polyterpenes, cyclic polyterpenes, such as terpene phenolic compounds.

Depending on the type of plant being treated, the formulation is added during watering and feeding in optimum doses during the vegetative growth, flowering, and fruit set and/or swell stages. The formulation appears to both enlarge the gland or trichome cell size and density, multiplying the amount of gland sites that produce terpenes and other essential oils on the surface area of a wide range of plant species, such that the synthesis of the native terpenoids is increased in the foliage, flowers and plant fruit.

Other aspects of the invention include a method of plant extraction of the bio-active compounds, as well as the culture of callus plant cells to generate higher concentration of the bio-active compounds for subsequent extraction.

The preferred compositions contain a range of bio-active compounds that activate and enhance trichome cell activity and density in broad range of plant species. The method of plant treatment is applicable to plants grown for essential oils, such as in perfume, edible herbs and flavoring or medicinal compounds, as well as fruits, such as citrus and grapes. Trichomes, being multicellular outgrowth on the surface of plants, are typically clusters of 10-12 cells, wherein when the novel compositions are applied according to the methods disclosed herein, the trichomes approximately double in size to about 20-24 cells.

Hence, application of the novel compositions disclosed below results in an increase in terpenoids in plant foliage and fruit, increased plant health and native disease resistance, increase root zone size, health and nutrient extraction efficacy. The healthier plants also permits a decreased use of organic and non-organic chemical pesticides.

The increase in terpene product in the treated plants also protects and prolongs the fragrance of dried plant foliage, fruits and flowers.

It has also been observed that treatment of fruit bearing plants with the inventive compositions, such as tomatoes and citrus, also results in an increase fruit size and fruit flavor intensity.

Hence, one aspect of the invention is a composition used to treat plants, which generally contains the following three types of components; one or more bio-active terpinoid pre-metabolite (s), a nutrient mixture containing one of more of carbohydrates, phosphorus, potassium and amino acids, at least one preservative component to prevent fermentation of the nutrients.

Preferred inventive compositions have a neutral pH and is compatible with other plant feeds through an entire growth cycle.

The preferred one or more bio-active terpinoid pre-metabolite (s) are derived from plant source, such as one or more of mango, citrus (including grapefruit), *Catharanthus roseus, Phaseolus vulgaris,* and *Pelargonium odoratissimum*. It should be understood that the scope of the invention also includes any synthetic equivalents of active compounds derived in the extraction processes described herein, whether currently known or subsequently discovered. Hence, such alternative bio-active pre-metabolites contain one or more of geranyl acetate, geraniol (geranyl), beta-sitosterol, alpha-amyrin, beta amyrin, carotenoid, geranyl acetate, alpha-humulene, and mevalonate kinase, and the like.

Alternatively, the bio-active pre-metabolites contain one or more of a compound selected from the group consisting of geraniol (geranyl) and mevalonate kinase.

The bio-active terpinoid pre-metabolites are preferably prepared by alcoholic extracts, and added to the resulting composition used to feed plants as alcoholic solutions or tinctures.

Preferred stabilizers in the compositions include EDTA, sorbitol, methyl paraben, potassium sorbate and the like.

It is also preferred that all components of the composition remain in solution, which is achieved through the order of mixing described in the example below, as well as the use of solubility promoting compounds which may also include yucca extract.

As the pre-metabolites increase the density and size of the trichome in plants, the terpene output is only increased if the plants is also feed with nutrients that support the potential increase in trichomes. Such plant nutrients include in preferred formulations carbohydrates, such as sugars, and more preferentially disassociated sugars, potassium compounds, phosphorus compounds, amino acids. More preferably, the amino acids selected from the group consisting of L-glycine, L-luecine, L-glutamine and L-cysteine. Alternatives include one or more of nicotinic acid, Thiamine HCl, and Pyroxidine HCl.

Other nutrients may include sodium ferric diethylenetriamine penta-acetate, as well as plant pigment extracts in alcohol. Such plant pigment extracts can be derived from the same plants as a byproduct of the pre-metabolite extraction, and are more preferably the heavier pigment residue of alcoholic soaking of plant matter.

A currently preferred composition is provided below in Table 1:

TABLE I

| Ingredient | Weight percentage |
|---|---|
| monopotassium phosphate | 4-10 |
| sulphate of potash | 10.5 |
| sucrose | 51 |
| L-glycine | 4.5 |
| d-calcium pantothenate | 4.5 |
| L-luecine | 4.5 |
| L-cysteine | 4.5 |
| sodium ferric diethylenetriamine pentaacetate | 0.5 |
| floral ethanol extract of mango extract | 2 |
| floral ethanol grapefruit and/or *citrus* extract | 2 |
| floral ethanol *Catharanthus roseus* extract | 2 |
| floral ethanol *Pelargonium odoratissimum* extract | 2 |
| ethylenediamine-tetra-acetic acid (EDTA) tetrasodium salt | 0.5 |
| Sorbitol | 2 |
| methyl paraben | 2 |
| potassium sorbate | 2 |
| Ethanol mix of extract pigments, including *yucca* extract | 1.5 |
| Total | 100 |

The composition of Table I is preferably formulated by steps A-I described in further detail below. However, to the extent various substitutes or alternatives described above are available for the various components of the composition of matter of Table I, steps A-C are merely a non-limiting experimental example. The floral extracts mango, citrus and geranium are alcoholic suspensions or tinctures, which may include some water, and are preferably prepared by the following step A. In step A, for floral extracts one first obtains pericarps, that is the tissue that surrounds the fruit including rind and pulp, and whole fruits for extraction process-grapefruit, mango, and rose geranium (*Pelargonium odoratissimum*), which are then preferably soaked in grain alcohol (ethanol) for one day, preferably at a ratio of about 1 parts by volume alcohol to 2 parts by weight plant material. The mixture of suspended plants solids in fluid is then brought to the boiling point of alcohol in round bottom flask is boiled for one minute. This mixture is then set aside to cool. After cooling, mixture is then centrifuged for 5 minutes at 75 G. One then decants the supernatant mixture into new round bottom flask to provide the floral extracts listed in Table I, leaving residue behind for extracting pigment ingredients, step B. The alcohol in the pigment retaining residue from decanting is removed in Buchi rotovap bath evaporator under vacuum pressure. The resultant mixture of pigments is now re-suspended or dissolved in pure alcohol at a ratio of 2 parts by volume residue to 1 part by volume ethanol, including the addition of 0.01% yucca extract. The above and other ingredients in Table I are then preferably mixed according the following process to maintain solubility and shelf life.

Another aspect of the invention is a method of cell extraction and propagation by cell culturing to produce higher concentrations of pre-metabolites that have been discovered to be particularly effective in the preferred compositions.

Step C is the preparation of a floral ethanol *Catharanthus roseus*, or alternatively *C. longifolius, C. ovalis, Vinca minor, Phaseolus vulgaris* and *Pelargonium odoratissimum* extract. In the preferred method of producing such an extract is illustrated in FIG. 1, as process 1000, in which callus cells are cultivated being rich in bio-active compounds.

Such a method 1000 involves the step illustrated in FIG. 1, which include in step 100 plant material of a predetermined plant species under goes maceration.

The stages of process 1000 described below preferably deploy the formulations in Table II.

TABLE II

| Ingredients | Preplasmolysis Media (steps 100.) | Enzyme Media (step 120.) | Rinse Media (steps 130) | Flotation Media (step 130) | Culture Media (step 140) | total in mg |
|---|---|---|---|---|---|---|
| $KNO_3H_{27}$ | 101 | 950 | | | 950 | 2001 |
| $KH_2PO_4$ | 33 | 85 | | | 85 | 203 |
| $MgSO_4 \cdot 7H_2O$ | | | | | | |
| $MgSO_4$ | 6000 | 90.5 | | | 90.5 | 6181 |
| $CaCl_2 \cdot H_2O$ | 1474 | 660 | 660 | 660 | 660 | 4114 |
| $Na_2EDTA$ | | 18.7 | | | 18.7 | 37.4 |
| $FeSO_4 \cdot 7H_2O$ | | 13.9 | | | 13.9 | 27.8 |
| $MnSO_4 \cdot 4H_2O$ | | 11.2 | | | 11.2 | 22.4 |
| $ZnSO_4 \cdot 7H_2O$ | | 5.3 | | | 5.3 | 10.6 |
| $H_3BO_3$ | | 3.1 | | | 3.1 | 6.2 |
| KI | | 0.4 | | | 0.4 | 0.8 |
| $NaMoO_4 \cdot 2H_2O$ | | 0.125 | | | 0.125 | 0.25 |
| $CoCl_2 \cdot 6H_2O$ | | 0.0125 | | | 0.0125 | 0.025 |
| $CuSO_4 \cdot 5H_2O$ | | 0.0125 | | | 0.0125 | 0.025 |
| KCL | | | 22000 | | | 22000 |
| Glycine | 2 | 1 | | | 1 | 4 |
| Nicotinic Acid | 0.5 | 0.25 | | | 0.25 | 1 |
| Pyridoxine HCl | 0.5 | 0.25 | | | 0.25 | 1 |
| Thiamine HCL | 0.1 | 0.05 | | | 10 | 10.15 |
| Inositol | | | | | 100 | 100 |
| Sucrose | | | | 171000 | 10000 | 181000 |
| Sorbitol | | | | | 50000 | 50000 |
| Glucose | | 18000 | | | 30000 | 48000 |
| Mannitol | 9000 | 73000 | | | | 82000 |
| Casein hydrolysate | | | | | 500 | 500 |
| Glutamine | | | | | 100 | 100 |
| Serine | | | | | 10 | 10 |
| Agar | | | | | | |
| (NAA)naphthalene acetic acid | | | | | 1.25 | 1.25 |
| 2,4-Dchlrophenoxy acetic acid | | | | | 0.25 | 0.25 |
| Zeatin plant hormone | | | | | 1 | 1 |
| Onozuka R10 cellulase (CAS 9012-54-8) | | 10000 | | | | 10000 |
| Onzuka R10 maceroenzyme (CAS 9032-75-1) | | 1000 | | | | 1000 |
| pH | 5.8 | 5.8 | 5.8 | 5.8 | 5.8 | |

In step 100, Maceration, one firsts obtain *Catharanthus* sp. *roseus, C. longifolius, C. ovalis, Vinca minor* and *Pelargonium odoratissimum* starts, then disinfects meristems, petioles, and leaves in 0.11% NaOHCl, and then using a presterilized erbacher blender, the preplasmolysis media of Table II, is added in sufficient quantity enough to cover plant parts, which are then mixed in 3 second blasts, waiting 20 seconds between each blast for plant parts to settle back to bottom of the blender. Depending on the scale of extraction and production, other equipment can be used to macerate the plant materials.

Then in step 110, Separation, using sterile colander (100 μm opening) one rinses off preplasmolysis media of Table II, using the rinse media of Table II, to capture the macerated plant debris retained by the colander.

Next in step 120, Enzymatic digestion of cellulosic material, one adds plant debris to enzyme mixture of Table II, putting the resulting mixture on rotary shaker, oscillating at 50 rpm overnight in the dark. The next day, one then decants off the remaining enzyme mixture. In the interest of consistency using variable plant materials, it is advisable to check for protoplast recovery via caclofluor white/epifluorescent microscope estimate the number of viable cells via hematocytometer and record in log book. Caclofluor stains the viable protoplast cells blue, which are precursors to the callus cells. Preferably the desired cell count at this stage is between about 500 to about 1000.

In step 130, Separation of protoplast cell, one takes harvested protoplasts recovered in step 120, and places them in 10 ml rinse media in centrifuge tubes, and then add 0.5 ml drops of flotation media to 10 ml rinse media and harvested protoplasts, insuring these drops go down side of test tube, until 3-5 mls of flotation media is visible as a separate band. Next, one centrifuges about 10 of such tubes for 10 minutes at 75 G. After centrifuging, one should gently harvest protoplasts with a sterile Pasteur pipette, as they will be evident as a green band in between the rinse and flotation media.

Next in step 140, Propagation of callus cells, the separated protoplast cells are propagated in a culture medium by mixing the harvested protoplasts in 2-3 ml of the liquid culture media of Table II, and this mixture is then placed on cell production harvester drum at 40-60 μmol/m²/s lux for an 18 hr photoperiod.

It is advisable to periodically inspect the above culture media, and after the first callus cell is seen, then transfer the same to new media for further development on the above harvester drum. Once the number of density of the callus cells have increased by a factor of about 2 from the pre-photoperiod diameter, they should be again transferred to a new media in cell culture vessel. This cell culture vessel is then placed on rotary shaker oscillating at 15 rpm for 40-60 µmol/m²/s lux for 18 hr photoperiod for 7-10 day. Once this cell culture vessel is filled with callus, the callus therein are harvested and prepared for extraction, step 150.

In step 150, Extraction of bio-active pre-metabolites, one takes the callus cell mixture from the cell culture vessel and freezes it in liquid nitrogen. The callus can be separated from the culture medium by filtration and rinsing with sterile DI water. The frozen product is then crushed in mortar and pestle to further macerate the cultured callus cells. One then takes the macerated callus cells and proceeds to extraction, taking equal parts diethyl ether and 90% ethanol, mixing it in a volume to weight ratio from the macerated callus of about 1 part solvent to 10 parts macerated callus cells. Then, deploying a rotovap in a buchi water bath, solvent is recovered, leaving an extract residue which can then be either mixed in the formulation of Table I, or frozen for up to about 2 years for subsequent mixing. This completes step 150, the extraction of bio-active pre-metabolites.

One should at the stage of protoplast culture, adjust the media pH as necessary, according to *Catharanthus* or other species extracted, to upward to pH 5.8 (preferably with 1N KOH solution).

Next in Step D of preparing the formulation of Table 1, in a large vessel filled with 115° F. water that is mixed with Lightning brand mixer, then the mono-potassium phosphate is added and let to dissolve, about 5 minutes. Next one adds sucrose and sorbitol which let dissolve (about 10 minutes). Next one adds sulphate of potash, which is let dissolve for about 15 minutes. In the next step, step E, to the above mixture one adds the L-luceine, L-glycine, L-cysteine, d-calcium pantothenate, which is left to mix for about 1 minute. Next, in Step F to mixture from step d-e one adds in 2 L erlenmeyer flask, 125° F. deionized water, then next one adds EDTA and Fe diacetate, which are then well mixed with a stir bar for about 10 minutes. When dissolved, one adds this solution to the mixture from step d-e, letting them mix together for at least about one minute. In Step g, one adds methylparaben and potassium sorbate, to this mixture, allowing them to mix together for about one minute.

Next in Step H, one now adds the prepared plant extracts from steps A-C, letting each mix for about one minute. In the last step I, one immediately bottles the resulting formulation.

The resulting formulation of step I is used to treat plants as follows, or alternatively, the formulation of Table 1 can be prepared using a different procedure in which a large vessel is filled with 115° F. water with a lightning brand mixer, to which is added the ethanol mix of plant pigments. Next one adds the potassium phosphate (which is optionally mono-, di- or tri-potassium phosphate), and the sulfate of potash, which are mixed to dissolve for about 20 minutes. Then, by drop wise addition of 1 N KOH the pH is reduced to about 5.5 After the pH is thus corrected, one adds glucose and the floral extracts and mixes them for another 10 minutes. Then one adds sodium ferric diethyl enetriamine pentaacetate to the mixture, and continues to mix for an additional ten minutes. Next one optionally adds sucrose, or optionally glucose or myoinositol, in its placing with continued mixing for about 10 minutes. The one adds methyl paraben, or optionally polypareben. After additionally mixing of 1-5 minutes, the pH is checked an adjusted upward to 6.0 with drop wise additions of 1N KOH solution. The resulting product is then bottled.

The bottled formulation of Table I is diluted in water that is used to irrigate plants, trees and vegetables, at further recommended below, but which is generally at a dilution of 15-30 ml/4 L. (1 Gal.) for the last 4-6 weeks of flowering. Further, the bottled formulation of Table I has been tested at higher concentrations with a large variety of nutrients and mediums—never with any results of burning or negative effects. Hence, it is optionally deployed as a feed component throughout the entire cycle of growth.

More specifically, for herbaceous annuals the formulation of Table I and its equivalents are preferably mixed at a concentration of about 2 mls/gallon of feeding water, and applied at this rate during vegetative stages of plant growth. When flowering occurs, it is recommended to increase the dosage rate to 8 ml/gallon. It is also recommended that once seed set initiates, use of the formulation is discontinued.

In contrast, for herbaceous perennials, one should add 5-15 mls per gallon during vegetative phased of growth, but apply this solution at every other watering. Once flowering initiates, the feed rate should be at every watering and adjusted to a steady rate of 10 mls/gallon. However, the feed rate can be increase during last three weeks of flowering, before seed set to 30 mls/gallon Use should be discontinued if seeds are set, as the objective is to harvest plants before any seed set.

In contrast, for woody perennials and vines, one adds 3-6 mls gallon every feeding during vegetative phases of growth. This is increase to about 15 mls/gallon during fruit set and swell. This feed solution is used every other feeding until fruit is ready to harvest. More specifically, for grapes, once fruit develops, the feed concentration is at 20 ml/gallon every other feeding.

In contrast, for woody trees one adds 5-15 mls/gallon during reproductive fruit set only. However, the dosage is then increased to 60 ml/gallon for the last four weeks of fruit development. More specifically, for pomaceous fruits, this solution should be fed every watering.

Another aspect of the invention is a process of plant treatment having the steps of extracting a bio-active pre-metabolite from a first plant species, then applying the extracted bio-active pre-metabolite to a second plant species, to either promote the health, productivity, flavor or taste thereof, or the output of terpenes and related compounds for extraction from the stems, bark, leaves, buds, flowers or fruits thereof. It should be appreciated that the bio-active pre-metabolites can be extracted from the stems, bark, leaves, buds, flowers or fruits of the first plant species.

Tests conducted with three pairs of spearmint plants, in which one in each pair is a control. The control and test plants were watered with the preferred formulation (30 ml/4 L (1 gal.) showed increase in menthol production of 7, 11 and 16%, and 69%. The plants were grown for 4 weeks from starts and watered 3×/7 days just until the soil was visibly saturated. The menthol concentration in the leaves was measured by extraction in methyl alcohol with the extract injected into a Gas Chromatograph equipped with a column calibrated for typical plant terpenoids.

Similar comparative testing was done with the OG Kush strain *Cannabis indica* using flowers from multiple plants grown and irrigated under the same conditions for 7 weeks, and showed increases in various terpenes of 8 to 15%, as shown below in TABLE III.

TABLE III

| Compound | test, ppm | control, ppm | % change |
|---|---|---|---|
| alpha-pinene | 1.21 | 1.09 | 11.3% |
| Sabinene | 2.10 | 2.10 | 0.0% |
| Linalool | 2.78 | 2.44 | 14.0% |
| alpha-Terpineol | 2.18 | 1.96 | 11.1% |
| beta-Caryophyllene | 3.16 | 2.80 | 13.0% |
| alpha-humulene | 1.49 | 1.30 | 15.0% |
| Nerolidol 2 | 2.50 | 2.29 | 9.0% |
| alpha-Bisabolol | 3.75 | 3.44 | 9.0% |
| Phytol 2 | 0.49 | 0.46 | 8.1% |

It should be appreciated that while synthetically prepared bio-active pre-metabolites can be used, another aspect of the invention is the extraction pre-metabolites from various plant or vegetative species that are different than the plant species to be treated with the composition.

Not wishing to be bound by theory, it is currently believed that the bio-active pre-metabolites act as the pre-cursors to plant oil production, via a combination of metabolic pathways that are energized by the bio-active compounds and the nutrients in the preferred compositions.

Figure 4:
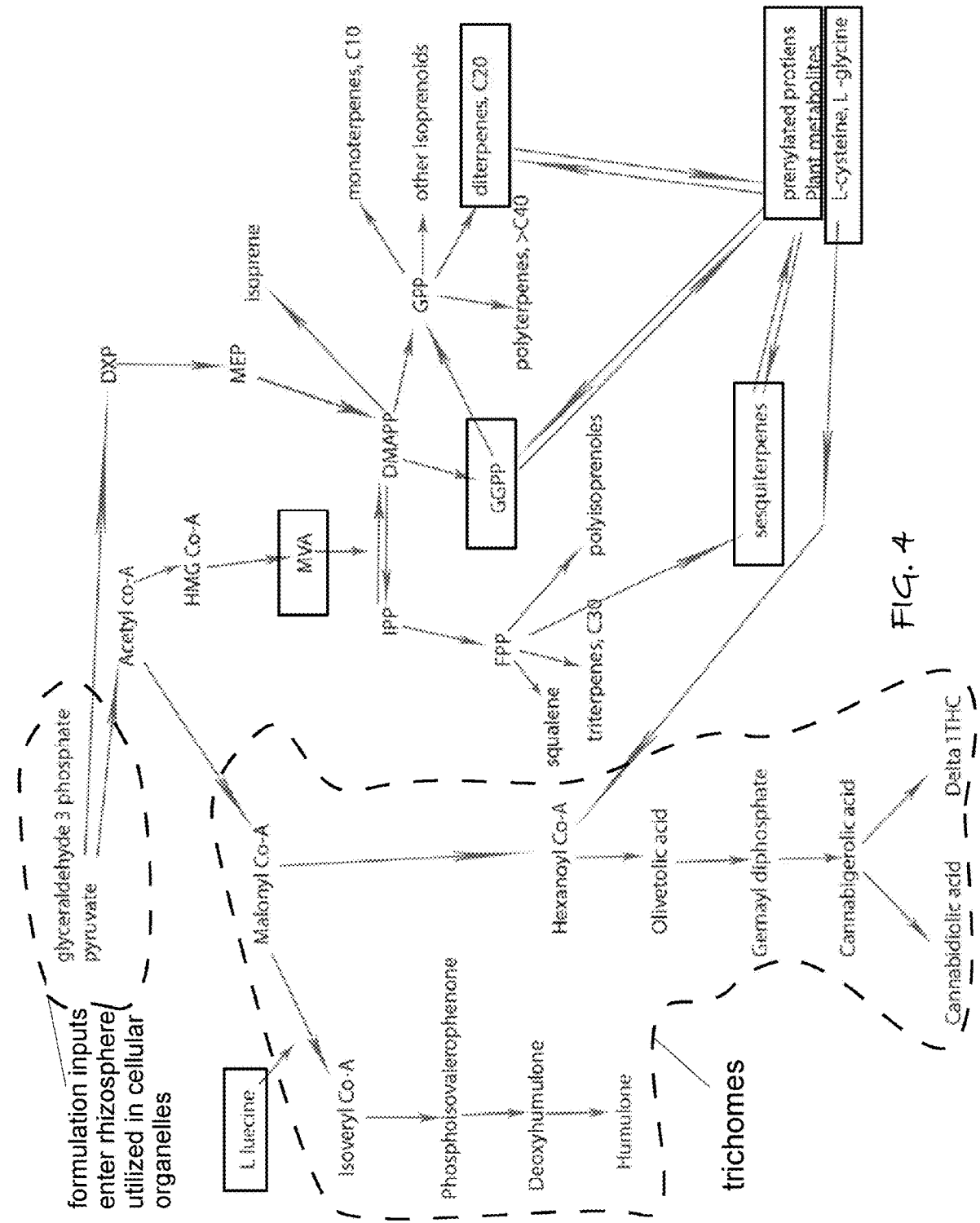
FIG. 4 is a summary of the metabolic pathways in plants believed to be stimulated by the preferred compositions.

FIG. 4 illustrates the isoprenoid (terpene/terpenoid) biosynthetic pathways as currently believed to be beneficially modulated by preferred compositions. Sets of adjacent bidirectional arrows indicate transport between contiguous plant cells. These are extremely generalized in that all of the chemical reactions are not included along the arrow paths. Some transport occurs back and forth between cells.

The following abbreviations have been used in the FIG. 4: DMAPP=dimethylallyldiphosphate; DXP=deoxyxylulose 5-phosphate; FPP=farnesyl diphsopahte; GGPP=geranylgeranyl diphosphate; GPP=geranyl diphsophate; HMG CoA=hydroxymethylglutary CoA; IPP=isopentyldiphosphate; MEP=methylerythritol 4-phosphate; and MVA=mevalonate (anion of melavonic acid).

It should be appreciated that while terpene synthesis generally occurs in trichome cells on the surface of plants leaves and flowers, an aspect of the invention is stimulating other metabolic processes in a plant to enable transport of the appropriate compounds in the formulations to the trichome cells. Pathways within trichome cells are indicated by a surrounded broken line boundary. Inputs from the preferred formulations are indicated by square boxes, as further explained below.

Hence, the diagram has been broken down to illustrate the trichome activity, as well as the activity in other cells from the uptake of water and nutrients necessary for vascular transport in the plant and transfer between contiguous plant cells.

The fractionated carbohydrates that are derived from the formulation protocol enhance respiration during low photosynthetic input during flowering. L-luceine is one of the amino acids in the formulation for *Humulus*, luceine catabolism is directly linked to the isoveryl co-A cytoplasmic reactions to form Phlorisovalerone which is an intracellular reaction.

MVA (mevalonate) is provided by the tissue culture extracts or synthetic equivalents from *Pelargonium, Catharanthus, Phaseolus*. Diterpenes, C20 are provided by mango/citrus extracts. GGPP is provided by the various isomers or synthetic equivalents in the plant tissue extracts.

The glyceraldehyde 3 phosphate/pyruvate reaction that occurs in the plant's cellular organelles is enhanced by the fractionated carbohydrates that are derived from the formulation protocol enhancing respiration during low photosynthesis input during flowering. Sesquiterpenes are provided by the mango and citrus extracts in the preferred formulations.

The gernayl diphosphate in the trichome cell synthetic pathways is provided by the plant extracts via tissue culture. However, it still must be transported from the rhizosphere to the plant vascular tissue, and then through vascular tissues to the plant trichomes.

Lipids in the mango, citrus, and tissue culture extracts are modified via prenylation of C15 and C20 isoprenoids. L-cysteine inputs exacerbate the covalent addition of these isoprenoids to the C terminus of proteins made by the plant in protein synthesis. This process helps promote membrane interactions of the formulation inputs so that the typical hydrophobic nature of the lipids involved are reduced, thus allowing greater facilitation of membrane to membrane reactions and increasing the formulation inputs into a plant's trichomes.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims.

I claim:

1. A process for plant production, the process comprising the steps of:
    a) providing an extract of a pre-metabolite of a bio-active compound from at least one of the buds, flowers, bark, foliage and fruit of a first plant species,
    b) applying a composition of matter containing the extract of the pre-metabolite to a second plant species during the growth thereof,
    c) harvesting at least one of the buds, flowers, bark, foliage and fruit of the second plant species, wherein the composition of matter comprises:
        i) an alcoholic extract of one of the buds, flowers, bark, foliage and fruit of *Catharanthus roseus, C. longifolius, C. ovalis, Vinca minor* and *Pelargonium odoratissimum*, and
        ii) a plant nutrient composition comprising one or more sources of carbohydrate in an amount sufficient to provide excess carbohydrate over that in the extract.

2. The process for plant production according to claim 1 wherein the composition of matter further comprises one or more alcoholic extracts of a plant selected from the group consisting of mango and citrus.

3. The process for plant production according to claim 1 wherein the composition of matter further comprises a plant enzyme.

4. The process for plant production according to claim 3 wherein the plant enzyme is mevalonate kinase.

5. The process for plant production according to claim 1 wherein the composition of matter further comprises a stabilizer selected from the group consisting of EDTA, sorbitol, methyl paraben and potassium sorbate.

6. The process for plant production according to claim 1 wherein the composition of matter further comprises one or more of sugars and disassociated sugars and potassium compounds, phosphorus compounds and amino acids.

7. The process for plant production according to claim 1 wherein the composition of matter further comprises one or more of sugars and disassociated sugars and potassium compounds, phosphorus compounds and one or more of L-glycine, L-leucine, L-glutamine and L-cysteine, nicotinic acid, thiamine HCl, and pyroxidine HCl.

8. A process for plant production, the process comprising the steps of:
   a. providing an extract of a pre-metabolite of a bio-active compound from at least one of the buds, flowers, bark, foliage and fruit of a first plant species,
   b. applying a composition of matter containing the extract of the pre-metabolite to a second plant species during the growth thereof,
   c. harvesting at least one of the buds, flowers, bark, foliage and fruit of the second plant species,
   d. wherein the composition of matter comprises:
      i. an alcoholic extract of one or more of the buds, flowers, bark, foliage and fruit of *Catharanthus roseus, C. longifolius, C. ovalis, Vinca minor* and *Pelargonium odoratissimum*,
      ii. a plant nutrient composition comprising one or more sources of carbohydrate, to provide excess carbohydrate over that in the floral extract,
      iii. one or more floral alcoholic extracts of a plant selected from the group consisting of mango and citrus, and
      iv. a stabilizer selected from the group consisting of EDTA, sorbitol, methyl paraben and potassium sorbate, and
      comprises yucca extract.

9. The process for plant production according to claim 8 further comprising the step of extracting one or more terpene compounds from the second plant species.

10. The process for plant production according to claim 2 further comprising the step of extracting one or more terpene compounds from the second plant species.

11. The process for plant production according to claim 1 wherein the composition of matter is applied during irrigation with water, and the amount of the composition of matter is initially applied at a first rate and then applied at second rate that is higher than the first rate.

12. The process for plant production according to claim 11 wherein the composition of matter is applied at the first rate during vegetative growth and before flowering occurs and then is applied at the second rate after flowering occurs.

13. The process for plant production according to claim 11 wherein the composition of matter is applied at the first rate during vegetative growth and at the second rate during the last three weeks of flowering before seed set.

14. The process for plant production according to claim 11 wherein the composition is applied the first rate during reproductive fruit set and then applied at the second rate during the last four weeks of fruit development.

15. The process for plant production according to claim 11 further comprising the step of extracting one or more terpene compounds from the second plant species.

16. A process for plant production, the process comprising the steps of:
   a) providing plant matter from a first plant species,
   b) enzymatically digesting cellulosic material of the plant matter from the first plant species to liberate protoplast cells,
   c) separating the protoplant cells from the digested cellulosic material,
   d) propagating the protoplast cells to create callus cells,
   e) extracting a pre-metabolite of a bio-active compound from the callus cells,
   f) applying a composition of matter containing the extracted pre-metabolite to a second plant species during the growth thereof,
   g) harvesting at least one of the buds, flowers, bark, foliage and fruit of the second plant species, wherein the composition of matter comprises;
      i) an alcoholic extract of one of the buds, flowers, bark, foliage and fruit of *Catharanthus roseus, C. longifolius, C. ovalis, Vinca minor* and *Pelargonium odoratissimum*, and
      ii) a plant nutrient composition comprising one or more sources of carbohydrate in an amount sufficient to provide excess carbohydrate over that in the extract.

17. The process for plant production according to claim 16 wherein the composition of matter further comprises one or more alcoholic extracts of a plant selected from the group consisting of mango and citrus.

18. The process for plant production according to claim 16 wherein the first plant species is one or more of *Catharanthus roseus, C. longifolius, C. ovalis, Vinca minor* and *Pelargonium odoratissimum*.

19. The process for plant production according to claim 16 wherein the composition of matter further comprises a plant enzyme.

20. The process for plant production according to claim 19 wherein the plant enzyme is mevalonate kinase.

* * * * *